United States Patent [19]
Norris

[11] Patent Number: 4,997,280
[45] Date of Patent: Mar. 5, 1991

[54] SPECTROPHOTOMETRIC INSTRUMENT WITH RAPID SCANNING DISTORTION CORRECTION

[75] Inventor: Karl Norris, Beltsville, Md.

[73] Assignee: NIRSystems Incorporated, Silver Spring, Md.

[21] Appl. No.: 413,063

[22] Filed: Sep. 27, 1989

[51] Int. Cl.$^5$ .......................... G01J 3/06; G01J 3/28; G01J 3/42
[52] U.S. Cl. .................................. 356/308; 356/328; 356/319; 364/498
[58] Field of Search ............... 356/326, 328, 333, 334, 356/307, 331, 332, 305, 308, 319, 321, 323–325; 364/498

[56] References Cited

U.S. PATENT DOCUMENTS 4,883,963  11/1989  Kemeny et al. ..................... 356/326
4,930,891  6/1990  Sato .................................... 356/326

FOREIGN PATENT DOCUMENTS 0250070  12/1987  European Pat. Off. ............ 356/326

*Primary Examiner*—F. L. Evans
*Assistant Examiner*—K. P. Hantis
*Attorney, Agent, or Firm*—Lane, Aitken & McCann

[57] ABSTRACT

In a spectrophotometric instrument, a system is provided to correct for distortion caused by rapid scanning of the spectrum. In the instrument, photodetectors detect light energy which is scanned through a spectrum at a rapid rate. An amplifier amplifies the output signal generated by the photodetectors. The output signal of the amplifier is sampled at increments and the samples are converted to digital values. A first derivative is determined from the digital values by subtracting from each value the value from the preceding increment. The first derivative values are multiplied times a constant selected to correct for the distortion and the resulting product values are added to the amplitude digital values to provide a set of corrected values representing the intensity detected by the photodetectors.

6 Claims, 2 Drawing Sheets

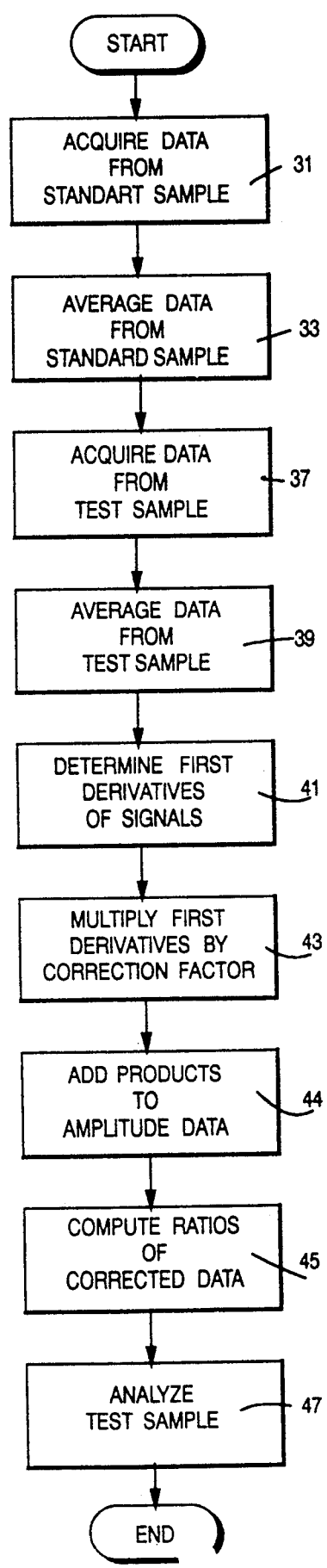
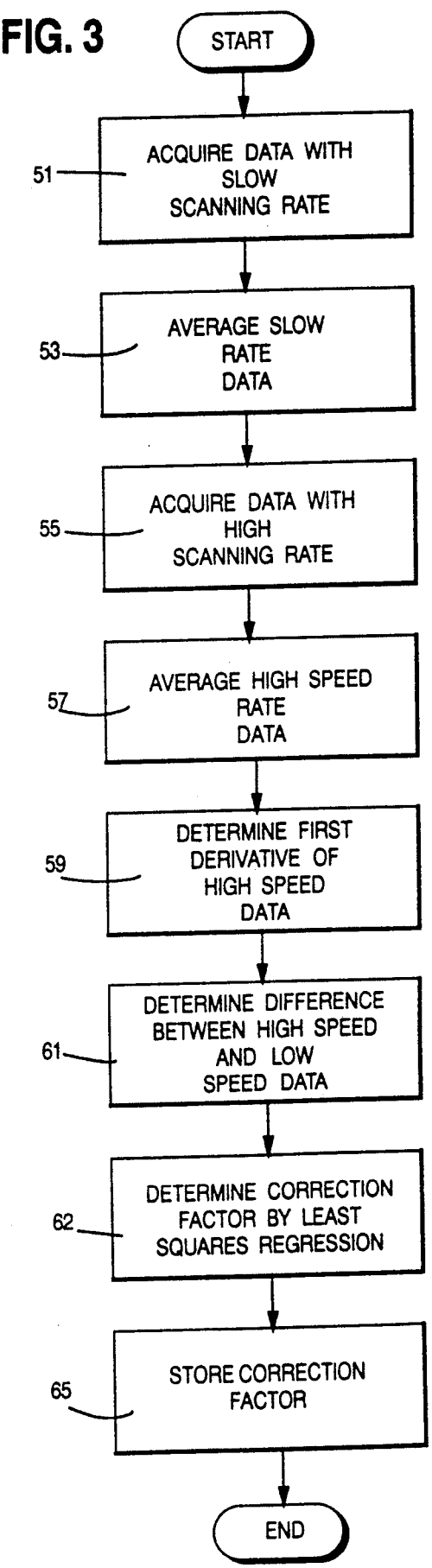

SPECTROPHOTOMETRIC INSTRUMENT WITH RAPID SCANNING DISTORTION CORRECTION

This invention relates to a spectrophotometric instrument of the type in which a narrow band of the spectrum is detected by a photodetector and this narrow band is rapidly scanned through the spectrum.

One type of instrument to which the present invention relates employs an optical grating, which receives light through an entrance slit and disperses the received light into a spectrum directed toward an exit slit. The optical grating is oscillated to rapidly scan the light transmitted through the exit slit through the spectrum dispersed by the grating. Such an instrument is disclosed in U.S. Pat. No. 4,285,596 to Isaac J. Landa. Another such instrument is disclosed in copending U.S. application Ser. No. 294,679 invented by Philip A. McGee and assigned to the assignee of the present invention. Alternatively, the present invention is also applicable to the instruments which employ filters, which are tilted as they pass through a light beam to scan the transmitted light through a spectrum. Such an instrument is disclosed in U.S. Pat. No. 4,040,747 to Donald R. Webster. Both types of instruments, the oscillating grating type and the tilting filter type, are advantageously employed operating over a spectrum covering the near infrared to analyze agricultural products, such as grain samples. Such instruments, by measuring the reflectivity of the sample at narrow wavelength increments operate to accurately determine the oil, protein, and water content of a grain sample as more fully set forth in the above mentioned Webster U.S. Pat. No. 4,040,747.

In the oscillating grating type instruments, such as those disclosed in the above mentioned Landa patent and McGee application, the narrow bandwidth of light, which is transmitted through the exit slit illuminates a sample to be analyzed. Light reflected from the sample is detected by photodetectors and the resulting photodetector signal is amplified and then converted to a sequence of digital values, each representing the energy reflected at an incremental point distributed along the spectrum being scanned as the grating oscillates. The digital values are applied to a computer, where they are received and are used to analyze the sample such as to determine the oil, protein, and water content of a grain sample.

A limit on how fast a spectrum can be scanned over the photodetector is determined by the response time of the photodetectors and the amplifier connected to amplify the output signal from the photodetectors. When the spectrum is scanned too rapidly, the output signal of the amplifier will fail to reach its equilibrium value at each incremental point at which the output value is converted to a digital value. As a result, the digital values received by the computer will be distorted and will fail to accurately represent the reflected energy from the sample at each increment of the spectrum at which the output signal from the amplifier is converted to a digital value.

SUMMARY OF THE INVENTION

In accordance with the present invention, the first derivative of the output signal from the amplifier is determined as the narrow wavelength band being received by the photodetector is scanned through the spectrum at a rapid rate faster than would normally be permitted by the response time of the photodetectors and amplifier. The first derivative is determined by subtracting from the output signal of the amplifier at each incremental point, the output signal of the amplifier at the preceding incremental point to determine a set of difference values representing the first derivative of the output signal at each incremental point. The difference values are determined by the digital computer and then each difference value is multiplied by a correction factor to determine a correction value for each incremental point on the spectrum for which a digital value representing reflectance is received. The correction values are then added to the digital values representing the amplifier output at each incremental point to provide a corrected set of values for each incremental point along the spectrum. By adding the fraction of the derivative to the amplifier output values, the system corrects for the distortion of the output signal caused by the rapid scanning. The corrected set of values are then employed in a conventional analysis of the sample. With the system of the invention, an accurate analysis of the sample is obtained even though the spectrum is scanned at a rate which is faster than that normally permitted for the response time of the photodetectors and the amplifier.

To determine the correction factor to be multiplied times each derivative value to determine the correction values, a standard sample is scanned by the instrument at a slow rate, that is sufficiently slow for the output signal of the amplifier each incremental point to reach the equilibrium value. The same sample is then scanned at a rapid rate, that is at the same rate that a test sample to be analyzed is to be scanned. The correction factor is then determined by least squares averaging from the data at several points distributed along the spectrum.

BRIEF DESCRIPTION OF THE DRAWINGS

FIG. 2 is a flow of a computer program employed in the computer of the instrument of FIG. 1 in accordance with the present invention; and FIG. 3 is a flow chart of a computer program used to determine a constant employed in the program of FIG. 2.

DETAILED DESCRIPTION OF A PREFERRED EMBODIMENT

Figure 1:
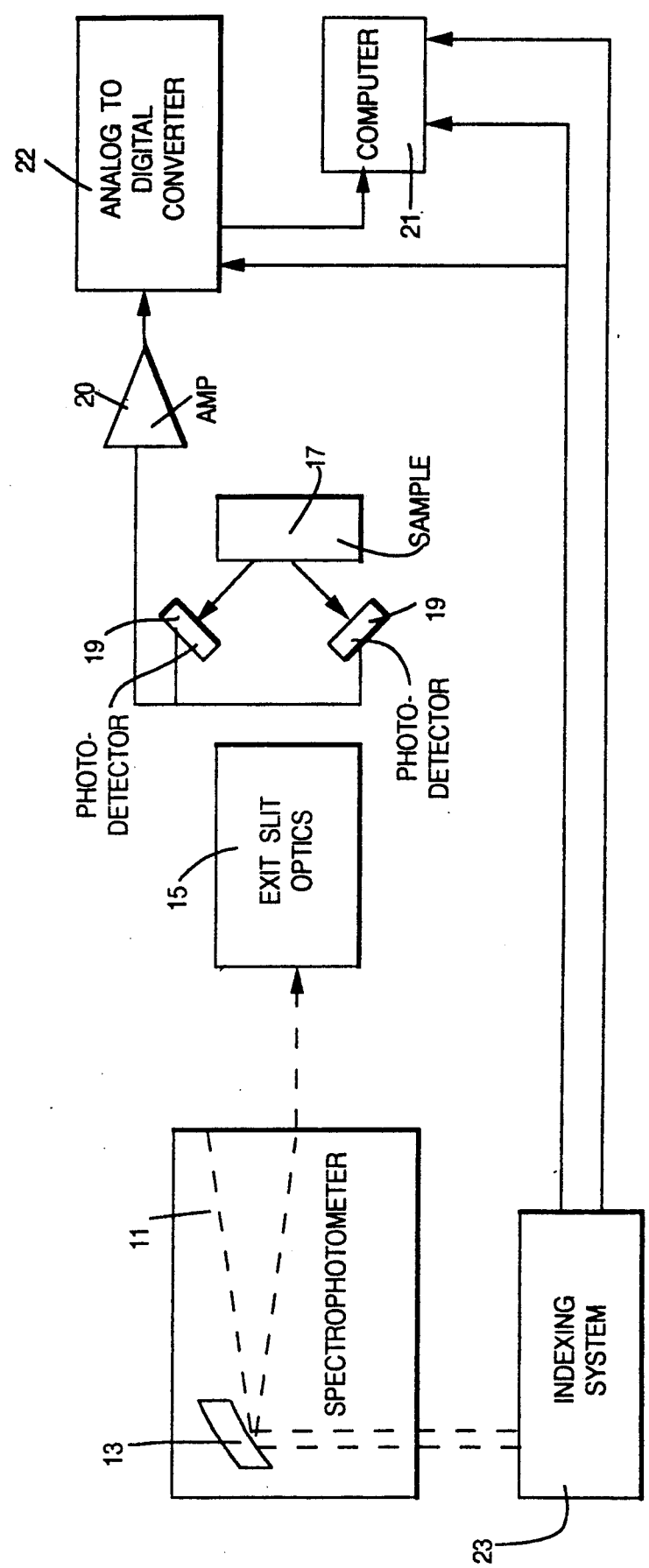
FIG. 1 schematically illustrates an example of an instrument in which the present invention is employed.

FIG. 1 schematically illustrates an instrument of the type to which the present invention is applicable. An example of such an instrument is disclosed in detail in the above mentioned copending U.S. application Ser. No. 294,679. As shown in FIG. 1, the instrument comprises a near infrared spectrophotometer 11 having an oscillating diffraction grating 13. The spectrophotometer 11 directs light with a narrow wavelength band through exit slit optics 15 to a sample 17. As the grating oscillates, the center wavelength of the light that irradiates the sample is swept through the near infrared spectrum. Light from the diffraction grating that is reflected by the sample 17 is detected by infrared photodetectors 19. Photodetectors 19 generate a signal that is transmitted to an analog-to-digital converter 22 by an amplifier 20. An indexing system 23 generates pulses as the grating 13 oscillates and applies these pulses to a computer 21 and to the analog-to-digital converter 22. In response to the pulses from the indexing system 23, the analog-to-digital converter converts successive samples of the output signal of the amplifier 20 to digital values, which are stored in the computer 21. Each digital value thus corresponds to the output of the amplifier 20 at a specific wavelength in the near infrared irradiating the sample. The computer 21 monitors the angular position of the grating 13, and accordingly, the wavelength irradiating the sample, as the grating oscillates, by counting the pulses produced by the indexing system 13. The pulses produced by the indexing system 13 define incremental index points, at which values of the output signal of the amplifier 20 are converted to digital values and stored in the computer 21. The index points are distributed incrementally throughout the near infrared spectrum, each index point corresponding to a different wavelength at which the sample is irradiated.

To analyze a test sample, data is acquired first from a standard sample and then data is acquired from the test sample. In accordance with the invention, the grating is oscillated at such a high rate that the output signal from the photodetectors 19, as well as from the amplifier 20 is distorted; that is these signals do not have time to reach their equilibrium values and accordingly, the output signal of the amplifier 20 does not correctly represent the reflected intensity from the sample 17.

In accordance with the present invention, a standard sample is repeatedly scanned at a high rate, for example 20 times to acquire 20 sets of data from the standard sample, each set of data comprising a set of digital values with each digital value of the set corresponding to the output signal from the amplifier at each incremental index point in the spectrum for one scan through the spectrum. As shown in the flowchart of FIG. 2, the program controlling the computer 22 in instruction sequence 31 acquires and stores the 20 sets of data from the standard sample as the standard sample is being scanned at a rapid rate. After the data from the standard sample is acquired, the program of the computer proceeds into instruction sequence 33 in which the data at each incremental index point in the 20 sets of data is averaged to get an average value for each incremental point. The standard sample receiving the light from the exit slit optics is then replaced by the test sample, that is the sample which is to be analyzed by the instrument. The grating 13 then again oscillated at a high rate to scan the light irradiating the test sample through the near infrared spectrum. This scanning is repeated 20 times so that the computer acquires and stores 20 sets of data from the test sample. This step of the program in FIG. 2 is represented by instruction sequence 37. Following the acquisition of the data from the test sample, the computer enters instruction sequence 39, in which it averages the values obtained from each incremental point in the 20 sets of data from the test sample to obtain an average value of the output signal from the amplifier 20 at each incremental point distributed throughout the infrared spectrum for the test sample.

Because the reflectivity of the samples vary throughout the spectrum and because the intensity of the narrow wavelength band passing through the exit slit also varies throughout the spectrum, the intensity of the reflected energy from the sample will vary up and down in a continuous curve as the grating scans the wavelength through the spectrum. The set of average values at each incremental point stored for the standard sample in instruction sequence 33 and stored for the test sample in instruction sequence 37 will represent incremental points along the continuous curves representing the average output signal of the amplifier 20 as the wavelength irradiating the sample is scanned through the near infrared spectrum.

Following the averaging step in instruction sequence 39, the program enters instruction sequence 41, in which the first derivative of the curve representing the variations in the signal from the amplifier 20 for the standard sample and the corresponding first derivative for the test sample are determined. To determine the value of the first derivative at a given incremental point in the spectrum, the average value from the immediately preceding point is subtracted from the average value at the incremental point. The difference represents the derivative at the incremental point. By carrying out this subtraction step for each incremental point, a set of difference values, one for each incremental point, is obtained in instruction sequence 39 for both the standard sample and the test sample. These sets of difference values represent the first derivatives of the curves which represent the variation in the average value of the corresponding output signal from the amplifier 20.

Following instruction sequence 41, the program enters instruction sequence 43, in which the difference values determined in instruction sequence 41 are each multiplied by times a correction factor. The resulting product is added to the average value representing the average output value from the amplifier 20 determined at the corresponding incremental point in instruction sequence 44. The resulting sum at each incremental point will represent the intensity of the reflected energy at the incremental point corrected for the distortion caused by the rapid scanning through the near infrared spectrum. This step of multiplying the difference values representing the first derivative times the correction factor and adding the resulting product back to the original average value obtained from the incremental point is done both for the averaged set of data from the standard sample and the averaged set of data from the test sample so as to obtain a corrected set of intensity values for both the standard sample and the test sample. The ratio of the corrected data from the test sample to the corrected data from the standard sample is then determined at each incremental point in instruction sequence 45. The resulting set of ratios will represent the reflectivity of the test sample at each incremental point. From the resulting ratios, the sample is analyzed in instruction sequence 47. For example, in a grain sample, the percentages of oil, protein, and water can be determined. The method of using the reflectivity data to determine the constituents of grain sample is disclosed in U.S. Pat. No. 3,861,788.

Another method of analyzing a sample by which a composition is identified or compared with another composition is disclosed in U.S. Pat. No. 4,766,551.

The program for computing the correction coefficient is shown in FIG. 3. As shown in FIG. 3, in the first instruction sequence 51 of the program, data is acquired from the standard sample by scanning the sample several times, e.g. 20 times at a slow rate, to obtain 20 sets of values, each set representing the intensities of reflection at the incremental points distributed throughout the infrared spectrum. The values obtained in step 51 are then averaged for each incremental point in instruction sequence 53 to obtain an average intensity value at each incremental point. Following this instruction sequence, in instruction sequence 55, data is acquired from the standard sample by scanning the standard sample at a high speed 20 times to obtain 20 sets of values, each set representing the output of the amplifier 20 at each of the incremental points as the light incident on the sample is scanned through the infrared spectrum. Following the acquisition of data by the high speed scan, the data obtained in instruction sequence 55 is averaged at each incremental point in instruction sequence 57 to obtain a set of average values representing the average output of the amplifier 20 at each of the incremental points during the high speed scan. Following instruction sequence 57, the program enters instruction sequence 59, in which the first derivative of the curve represented by the average values obtained in instruction sequence 57 is determined. This step is carried out by subtracting from each value the value at the preceding incremental point to obtain a difference value. Following instruction sequence 59, the program enters instruction sequence 61, in which the program computes the difference between the average data values obtained in instruction sequence 53 from the average values at the same points in the data obtained in instruction sequence 57 at five selected incremental points. The average intensity values determined in instruction sequence 53 are assumed to represent the undistorted values of the reflected intensity at each incremental point. Using these five difference values obtained in instruction sequence 61 and the values of the first derivative computed during the instruction sequence 59 at the same incremental points, the correction factor to be used in the program of FIG. 2 is computed by least squares regression in instruction sequence 62. In this computation, the formula for computing the correction factor is as follows:

$$K = \frac{5 \sum_{n=1}^{5} X_n Y_n - \left(\sum_{n=1}^{5} X_n\right)\left(\sum_{n=1}^{5} Y_n\right)}{5 \sum_{n=1}^{5} X_n^2 - \left(\sum_{n=1}^{5} X_n\right)^2}$$

In the above formula, the correction factor is represented by K, the first derivative values at the five selected points are represented by $X_1$ through $X_5$, the difference values at each of the five selected points determined in instruction sequence 61 are represented by $Y_1$ through $Y_5$. When this correction coefficient has been computed, it is stored in the computer memory in instruction sequence 65.

When the correction factor has been computed and stored in the memory for a given high speed scanning rate, the instrument may be repeatedly analyze samples at the high speed scanning rate, at which the output of the amplifier 20 would be considerably distorted and accurate values of reflectivity of the instrument at each of the incremental points on the spectrum will be obtained. The degree of distortion correction achieved by the invention can be appreciated by observing the reduction in the shift in the output signal peaks produced in response to reflected energy peaks from a calibration sample. When a typical instrument is operated at about four times the rate at which accurate measurements can be made, a peak in the output signal will be shifted an apparent 0.75 nanometers from the wavelength at which the peak in reflected intensity occurs. When the distortion is corrected in accordance with the present invention, the apparent waveshift is reduced to 0.09 namometers.

In the preferred embodiment as described above, the detected energy is described as being reflected from the sample to be analyzed. Alternatively, the energy may be transmitted through the sample. The system for carrying out the computation to correct the distortion is described as a digital system in the preferred embodiment. Alternatively, the correction can be carried out by analog circuitry components. In an analog system, analog circuits would determine the first derivative, multiply the first derivative times a correction factor and add the resulting product to the amplifier output as the wavelength is being scanned through the spectrum. Instead of irradiating the sample with the output from the spectrophotometer, the sample can be irradiated with constant wide band light and the light transmitted through or reflected from the sample applied to the spectrophotometer. These and other modifications of the preferred embodiment of the invention may be made without departing from the spirit and the scope of the invention, which is defined in the appended claims.

I claim:

1. A spectrophotometric instrument comprising spectroscopic means to rapidly scan the wavelength of a narrow wavelength band of light through a predetermined spectrum, photodetecting means to detect the intensity of the energy in said band throughout said spectrum and generate an output signal in response thereto, said spectroscopic means scanning the wavelength of said band at a sufficiently rapid rate relative to the response time of said photodetecting means that there is substantial distortion in the output signal of said photodetecting means relative to the intensity of the energy in the detected narrow wavelength band, and means responsive to the output signal of said photodetecting means to correct the output of said photodetecting means for said distortion by determining the first derivative of the variation in the output of said photodetecting means as said wavelength is scanned through said spectrum, multiplying said first derivative by a predetermined constant, and adding the resulting product to the output of said photodetecting means.

2. A spectrophotometric instrument comprising spectroscopic means as recited in claim wherein said means responsive to the output of said photodetecting means comprises computer means to (1) determine a value representing the amplitude of the output signal of said photodetecting means at each of a multiplicity incremental points distributed throughout said spectrum, (2) subtract from the value determined at each incremental point the value determined at the immediately preceding incremental point to determine a set of difference values, one for each incremental point, and representing the first derivative of the output signal of said photodetecting means, (3) multiply each of said difference values times said predetermined constant to determine a set of products, one for each incremental point, and (4) add each of said products to the corresponding value representing the output of said photodetecting means to determine a corrected value of the energy detected by said photodetecting means at each incremental point.

3. A spectrophotometric instrument as recited in claim 1, wherein the intensity of energy detected by said photodetecting means is reflected from a sample.

4. A method of operating a scanning type spectrophotometric instrument of the type which scans the wavelength of a narrow wavelength band of light detected by photodetecting means through a predetermined spectrum, wherein said photodetecting means generates an output signal in response to the intensity of the light energy detected, comprising the steps of scanning said wavelength through said spectrum at a sufficiently rapid rate that the output signal of said photodetecting means is distorted relative to the intensity of the light energy detected by said photodetecting means, determining the first derivative of the output signal of said photodetecting means as it varies through said spectrum, multiplying said first derivative times a constant selected to correct for said distortion, and adding the resulting product to the value of the output signal of said photodetecting means.

5. A method as recited in claim 4, wherein said step of determining the derivative of the output signal of said photodetecting means comprises determining the value of the amplitude of the output signal of said photodetecting means at each of a multiplicity of incremental points distributed throughout said spectrum, subtracting from the value determined at each incremental point the value determined at the immediately preceding incremental point to determine a set of difference values, one for each incremental point, multiplying each of said difference values times said correction factor, and adding the resulting product determined for each incremental point to the value determined for the amplitude of the output signal of said photodetecting means at such incremental point.

6. A method of analyzing a test sample comprising irradiating said test sample with a narrow wavelength band of light, rapidly scanning the wavelength of said narrow wavelength band through a predetermined spectrum, detecting the intensity of the light energy reflected from said sample with photodetecting means and generating an output signal in response thereto, said step of scanning being at a sufficiently rapid rate that the output signal of said photodetecting means is substantially distorted relative to the intensity of light energy detected by said photodetecting means, determining the first derivative of the output signal of said photodetecting means, multiplying said first derivative times a constant selected to correct for said distortion, and adding the resulting product to the value of the amplitude of the output signal of said photodetecting means.

* * * * *

UNITED STATES PATENT AND TRADEMARK OFFICE
CERTIFICATE OF CORRECTION

PATENT NO. : 4,997,280
DATED : March 5, 1991
INVENTOR(S) : Karl Norris It is certified that error appears in the above-identified patent and that said Letters Patent is hereby corrected as shown below:

Column 6, line 41 (claim 2, line 2), after "claim", insert --1,--.

Signed and Sealed this

Seventeenth Day of November, 1992

Attest:

DOUGLAS B. COMER

*Attesting Officer*   Acting Commissioner of Patents and Trademarks